(12) United States Patent
Kingman et al.

(10) Patent No.: US 9,375,759 B2
(45) Date of Patent: Jun. 28, 2016

(54) MICROWAVE APPLICATOR

(71) Applicant: TECHNOLOGICAL RESOURCES PTY. LIMITED, Brisbane, QLD (AU)

(72) Inventors: Samuel Kingman, Burton on Trent (GB); Georgios Dimitrakis, Nottingham (GB); Christopher Dodds, Nottingham (GB)

(73) Assignee: Technological Resources Pty. Limited, Brisbane (AU)

( * ) Notice: Subject to any disclaimer, the term of this patent is extended or adjusted under 35 U.S.C. 154(b) by 0 days.

(21) Appl. No.: 14/356,044

(22) PCT Filed: Nov. 8, 2012

(86) PCT No.: PCT/AU2012/001360
§ 371 (c)(1),
(2) Date: May 2, 2014

(87) PCT Pub. No.: WO2013/067574
PCT Pub. Date: May 16, 2013

(65) Prior Publication Data
US 2014/0291212 A1    Oct. 2, 2014

(30) Foreign Application Priority Data

Nov. 8, 2011  (AU) ................................ 2011904637

(51) Int. Cl.
*B07C 5/34*   (2006.01)
*B07C 5/344*  (2006.01)
*H05B 6/70*   (2006.01)
*H05B 6/78*   (2006.01)
*H05B 6/80*   (2006.01)

(Continued)

(52) U.S. Cl.
CPC . *B07C 5/344* (2013.01); *B07C 5/34* (2013.01); *H05B 6/70* (2013.01); *H05B 6/784* (2013.01); *H05B 6/80* (2013.01); *B03B 1/02* (2013.01); *G01N 22/00* (2013.01)

(58) Field of Classification Search
CPC ....... B03B 1/02; B07C 5/3425; H05B 6/6402
USPC .................. 209/3, 11, 552, 576, 577; 250/253
See application file for complete search history.

(56) References Cited

U.S. PATENT DOCUMENTS 4,631,380 A * 12/1986 Tran ............................. 219/697
5,209,355 A *  5/1993 Mindermann .................. 209/3.1

(Continued)

FOREIGN PATENT DOCUMENTS

GB       2198242 A  *  6/1988  ............. G01N 22/00

OTHER PUBLICATIONS

International Search Report and Written Opinion dated Feb. 1, 2013 (PCT/AU2012/001360); ISA/AU.

(Continued)

*Primary Examiner* — Joseph C Rodriguez
(74) *Attorney, Agent, or Firm* — Banner & Witcoff, Ltd.

(57) ABSTRACT

A microwave radiation applicator for exposing mined material to microwave radiation is disclosed. The applicator includes side walls 3 and end walls 5 that define a chamber. One end wall has an opening that forms an inlet for mined material to be supplied to the chamber and the other end wall has an opening that defines an outlet for mined material to be discharged from the chamber. The side walls define a pentagon in transverse cross-section.

18 Claims, 8 Drawing Sheets

(51) Int. Cl.
*B03B 1/02* (2006.01)
*G01N 22/00* (2006.01)

(56) References Cited

U.S. PATENT DOCUMENTS

| | | | |
|---|---|---|---|
| 5,834,744 A * | 11/1998 | Risman | 219/697 |
| 6,112,903 A * | 9/2000 | Kimmel et al. | 209/11 |
| 6,462,320 B1 | 10/2002 | Fuls et al. | |
| 6,845,869 B1 * | 1/2005 | Graf von Deym et al. | 209/522 |
| 7,541,557 B2 * | 6/2009 | Voloshyn et al. | 209/576 |
| 8,410,397 B2 * | 4/2013 | Lovshin | 219/121.85 |
| 8,752,709 B2 * | 6/2014 | Harding et al. | 209/11 |
| 2010/0263482 A1 | 10/2010 | Liubakka et al. | |
| 2013/0186992 A1 * | 7/2013 | Wellwood et al. | 241/68 |

OTHER PUBLICATIONS

International Preliminary Examination Authority report under Chapter II dated Jan. 9, 2014 (PCT/AU2012/001360); IPEA/AU.

* cited by examiner

MICROWAVE APPLICATOR

CROSS-REFERENCE TO RELATED APPLICATIONS

The present application is a U.S. National Phase filing of International Application No. PCT/AU2012/001360, filed on Nov. 8, 2012, designating the United States of America and claiming priority to Australian Patent Application No. 2011904637, filed Nov. 8, 2011, and this application claims priority to and the benefit of the above-identified applications, which are both incorporated by reference herein in their entireties.

TECHNICAL FIELD

The present invention relates to an applicator for exposing material to microwave radiation.

The term "applicator" is understood herein to mean an apparatus that defines a chamber in which a material can be exposed to microwave radiation in a controlled manner.

The term "microwave radiation" is understood herein to mean electromagnetic radiation having frequencies in a range of 100 MHz to 10 GHz.

The present invention relates more particularly, although by no means exclusively, to an applicator for exposing fragments of mined material to microwave radiation for use in a method and an apparatus for processing mined material.

The term "mined" material is understood herein to include metalliferous material and non-metalliferous material. Iron-containing and copper-containing ores are examples of metalliferous material. Coal is an example of a non-metalliferous material. The term "mined" material is understood herein to include, but is not limited to, (a) run-of-mine material and (b) run-of-mine material that has been subjected to at least primary crushing or similar size reduction after the material has been mined and prior to being sorted. The mined material includes mined material that is in stockpiles.

The present invention relates particularly, although by no means exclusively, to a high throughput method and an apparatus for processing mined material to facilitate subsequent recovery of valuable material, such as valuable metals, from the mined material.

The present invention also relates particularly, although by no means exclusively, to a method and an apparatus for recovering valuable material, such as valuable metals, from mined material that has been processed as described above.

BACKGROUND ART

The applicant is developing an automated sorting system for mined material. The applicant is also developing a system for forming microfractures in mined material. Both systems expose mined material (on a fragment-by-fragment basis or on a bulk basis) to microwave radiation to facilitate downstream processing of the fragments.

In general terms, the method of sorting mined material being developed by the applicant as part of the automated sorting system includes the following steps:

(a) exposing mined material (on a fragment-by-fragment basis or on a bulk basis) to microwave radiation and heating the mined material, (b) detecting fragments of the mined material after the mined material has been exposed to microwave radiation, (c) using detected data and assessing the fragments on the basis of composition (including grade of a valuable metal) or texture or another characteristic of the fragments, and (d) physically separating fragments based on the assessment in step (c).

The purpose of exposing mined material to microwave radiation is to cause a change in the mined material that provides information on characteristics of the mined material that is helpful for sorting and ultimately downstream processing of fragments of the mined material and that can be detected by one or more than one sensor. The information may include any one or more of the characteristics of composition (including grade of a valuable metal), mineralogy, hardness, porosity, structural integrity, dielectric properties, and texture of the mined material.

The term "fragment" is understood herein to mean any suitable size of mined material having regard to materials handling and processing capabilities of the apparatus used to carry out the method and the downstream processing requirements. In the context of ore sorting, relevant factors include issues associated with detecting sufficient information to make an accurate assessment of the mined material in the fragment. It is also noted that the term "fragment" as used herein may be understood by some persons skilled in the art to be better described as "particles". The intention is to use both terms as synonyms.

Automated ore sorting technology known to the applicant is limited to low throughput systems, typically less than 100 tonnes/hr. The general approach used in these low throughput sorting systems is to convey ore fragments through sorters on a horizontal belt. The applicant has realised that there is a number of issues to be addressed in developing higher throughput automated sorting systems.

One issue for the technology development path of the applicant relates to ensuring that all of the mined material being processed is exposed to at least a minimum power density, i.e. the amount of energy per $m^3$ in the heated phase, to provide an accurate basis on which to assess the fragments of the mined material to allow sorting of the mined material into an "accepts" category and a "rejects" category that are above and below a threshold assessment parameter, respectively. Grade of a valuable metal is one example of a threshold parameter. An added dimension to this issue is to expose mined material to microwave radiation at high throughputs. A further dimension to this issue in a number of commercially important situations is to expose mined material having low concentrations of valuable material to microwave radiation and obtain a response to the microwave radiation that can provide an accurate basis on which to assess the fragments of the mined material.

The system for forming microfractures in fragments of mined material being developed by the applicant includes exposing fragments to electromagnetic radiation such as microwave radiation to form microfractures in the fragments. The microfractures facilitate downstream processing of the fragments to recover valuable material, such as valuable metals, from the fragments. The downstream processing options include, by way of example, heap leaching, with the microfractures allowing leach liquor to penetrate the fragments and improve recovery of valuable metals. Another downstream processing option includes comminuting the fragments and forming smaller fragments, processing the smaller fragments in a flotation circuit and forming a concentrate and smelting the concentrate to recovery valuable metals. As is the case with ore sorting technology discussed above, the technology for forming microfractures in fragments of mined material known to the applicant is limited to low throughput systems.

An issue for the technology development paths of the applicant in the fields of sorting fragments and forming micro-fractures in fragments relates to ensuring that all of the mined material being processed is exposed to at least a minimum power density of electromagnetic radiation that is required for downstream processing of the fragments.

Rectangular box-shaped, i.e. cuboid, microwave radiation heating applicators that have side walls that define a chamber that is rectangular in transverse cross-section and in longitudinal cross-section are a proven and tested design that is used extensively in domestic microwave heating applications. These applicators are hereinafter referred to as "rectangular applicators".

The inventors have found that such rectangular applicators have features that could be advantageous when applied to applicators for use in processing mined material at high throughputs, for example by exposing mined material to microwave radiation in automated sorting systems and forming microfractures in fragments of mined material. The features include ease of design, low electric field strength leading to reliable power delivery, ease of impedance matching, and large size.

However, the inventors have also found that rectangular applicators have disadvantages including low supported power density in a heated phase, very heterogeneous power density distribution, and difficulties in vapour extraction. As a consequence, the inventors have concluded that rectangular applicators are not suitable for the automated sorting system and the microfracturing system being developed by the applicant.

The above description is not to be taken as an admission of the common general knowledge in Australia and elsewhere.

SUMMARY OF THE DISCLOSURE

The inventors have carried out research and development work into applicator designs and have invented an applicator that has side walls that define a chamber that is a pentagon in transverse cross-section, hereinafter referred to as a "pentagonal applicator", which has the advantages of rectangular applicators and does not have the disadvantages of power density variation and vapour extraction of rectangular applicators mentioned above.

More particularly, the inventors have found that the pentagonal shape of the pentagonal applicator makes it possible to expose mined material in the chamber to a substantially uniform electric field and hence substantially uniform power density within the chamber as the material moves through the chamber.

In addition, the inventors have found that the pentagonal shape of the pentagonal applicator makes it possible for substantially all of the fragments of mined material to be exposed to at least a minimum power density to provide an accurate basis on which to assess the fragments to allow sorting of the mined material by the time mined material reaches an outlet end of the applicator.

In addition, the inventors have found that this performance of the pentagonal applicator of the present invention applies to variable feed materials and to larger sized applicators required for processing high throughputs of material. Therefore, the pentagonal applicator of the present invention is well suited for treating high throughputs of mined material with variable feed properties.

According to the present invention there is provided a chamber of a microwave radiation applicator in which material may be exposed to microwave radiation, the chamber being a pentagon in transverse cross-section.

According to the present invention there is provided a microwave radiation applicator for exposing mined material to microwave radiation for heating the mined material, the applicator including side walls and end walls that define a chamber, with one end wall having an opening that forms an inlet for mined material to be supplied to the chamber and the other end wall having an opening that defines an outlet for mined material to be discharged from the chamber, and with the side walls defining a pentagon in transverse cross-section.

The pentagon in transverse section may be a regular pentagon, i.e. with the side walls having the same dimensions.

The pentagon in transverse section may be an irregular pentagon, i.e. with the side walls having different dimensions.

The applicator may include an aperture to allow transmission of microwave radiation into the chamber.

The applicator may include a waveguide for transmitting microwave radiation from a microwave radiation generator to the aperture.

The applicator may include a plurality of apertures so that the applicator can operate as a multimode applicator.

The applicator may include a plurality of waveguides for transmitting microwave radiation from a microwave radiation generator into the chamber via the apertures.

The apertures may be in one of the side walls.

The apertures may be in more than one of the side walls.

There may be two apertures/waveguides. In other situations there may be three or more apertures/waveguides.

The waveguides may be offset with respect to each other along the length of the applicator.

The waveguides may be offset with respect to each other in terms of the orientation of the waveguides. For example, the waveguides may be perpendicular to each other. By way of particular example, one waveguide may be horizontal and another waveguide may be vertical.

The position of the apertures in relation to a path of movement of material through the applicator from the inlet to the outlet may be selected so that, in use, by the time fragments of mined material reach an outlet end of the applicator, substantially all of the fragments of material are exposed to at least a minimum power density or minimum total energy to provide an accurate basis on which to assess fragments to allow sorting of fragments.

The position of the apertures in relation to a path of movement of mined material through the applicator may be selected so that, in use, mined material is exposed to a uniform electric field and therefore a uniform power density as it moves through the chamber.

When the applicator includes a plurality of apertures and a plurality of waveguides associated with the apertures, the waveguides may be arranged at different orientations (for example along the length of the applicator or at different angles to each other) so that, in use, mined material is exposed to a uniform electric field and therefore a uniform power density as it moves through the chamber.

The applicator may include ventilation apertures in the side walls and/or the end walls to allow air flow through the chamber. The air flow may be helpful particularly from the perspective of removing moisture produced in the chamber.

The applicator may be any suitable length and any suitable transverse cross-sectional area. It is noted a key factor in the selection of the size of the applicator is the operating frequency of the microwave radiation for the applicator. The size is a function of the operating frequency of the microwave radiation for the applicator. As radiation frequency decreases and wavelength increases, the applicator must also become bigger. The embodiments of the applicator in accordance with the present invention shown in FIGS. 3 and 5/6 were designed to operate at 922 Mhz. When applicators with different operating frequencies are required, the optimum dimensions for the applicator can be determined by scaling the dimensions of the embodiments shown in FIGS. 3 and 5/6 based on the ratios of the new frequencies to 922 Mhz.

The applicator may be at least 250 mm long.
The applicator may be at least 300 mm long.
The applicator may be at least 500 mm long.
The applicator may be at least 1 m long.
The applicator may be at least 1.25 m long.
The transverse cross-sectional area of the applicator may be at least 0.5 m$^2$.
The transverse cross-sectional area may be at least 1 m$^2$.
The transverse cross-sectional area may be at least 1.25 m$^2$.

According to the present invention there is also provided an apparatus for processing mined material that includes the above-described microwave radiation applicator.

According to the present invention there is also provided an apparatus for microfracturing mined material that includes the above-described microwave radiation applicator.

According to the present invention there is also provided an apparatus for sorting mined material that includes the above-described microwave radiation applicator for heating mined material, a materials handling arrangement for transporting fragments of mined material through the chamber of the applicator via the inlet in one end wall and the outlet in the other end wall, a microwave radiation generator for generating microwave energy to be supplied to the chamber of the applicator, a detector for detecting fragments of mined material after exposure to microwave radiation in the chamber, a means for analysing data from the detector and assessing one or more than one characteristic of fragments, and a means for separating fragments on the basis of the analysis.

The characteristics may include composition (including grade of a valuable metal), mineralogy, hardness, porosity, structural integrity, dielectric properties, and texture of the mined material.

The position of the materials handling arrangement for transporting material within the chamber and the position of the apertures in relation to the transport arrangement may be selected so that, in use, by the time mined material reaches an outlet end of the applicator, substantially all of the fragments of mined material are exposed to at least a minimum power density or minimum total energy to provide an accurate basis on which to assess the fragments to allow sorting of mined material.

The position of the materials handling arrangement for transporting material within the chamber and the position of the apertures in relation to the transport arrangement may be selected so that, in use, mined material is exposed to a uniform electric field and therefore a uniform power density as it moves through the chamber.

The applicator may be arranged so that, in use the materials handling arrangement for transporting material within the chamber transports fragments of mined material horizontally through the applicator.

With this arrangement of the applicator, in a situation where there is a single aperture, the aperture may be above or below the materials handling arrangement.

With this arrangement of the applicator, in a situation where there is a plurality of apertures, the apertures may be either above or below the materials handling arrangement.

With this arrangement of the applicator, in a situation where there is a plurality of apertures, the apertures may be above and below the materials handling arrangement.

One advantage of locating the single aperture or plural apertures below the materials handling arrangement is to minimise dust from fragments of mined material blocking any aperture.

With this arrangement of the applicator, the side walls of the applicator may include a horizontal upper side wall, an upper pair of side walls extending outwardly and downwardly from opposite side edges of the upper side wall, and a lower pair of side walls extending inwardly and downwardly from the upper pair of side walls and meeting at lower side edges of the side walls.

Alternatively, with this arrangement of the applicator, the side walls of the applicator may include a horizontal lower side wall, a lower pair of side walls extending outwardly and upwardly from opposite side edges of the lower side wall, and an upper pair of side walls extending inwardly and upwardly from the lower pair of side walls and meeting at upper side edges of the side walls.

With this arrangement of the applicator, the materials handling arrangement may include a belt for transporting mined material to be exposed to microwave radiation through the chamber. With a belt, the mined material may be transported as separate fragments on the belt or as a bed of mined material.

The belt may be made from a microwave radiation transparent material.

The belt may be at least 500 mm wide.
The belt may be at least 1 m wide.

The apparatus may include a choke upstream and a choke downstream respectively of the inlet and the outlet in the end walls to prevent microwave radiation from escaping the chamber.

The applicator may also be arranged so that, in use, fragments of mined material can be transported vertically or at an angle to the vertical through the applicator.

With this arrangement of the applicator the side walls may be vertical or angled side walls and one end wall may be an upper end wall and the other end wall may be a lower end wall.

With this arrangement of the applicator the materials handling arrangement of the apparatus may include an applicator tube for transporting a bed of fragments of mined material downwardly through the chamber from the upper end wall to the lower end wall, and the applicator tube physically separating fragments moving through the applicator from the chamber so that the materials handling requirements for fragments in the applicator are at least substantially independent of the microwave radiation exposure requirements for the applicator.

The term "bed" is understood herein to mean that adjacent fragments in the bed are in contact with each other.

In use of the applicator tube, fragments of mined material are processed in the applicator on a bulk basis—as opposed to a fragment by fragment basis. More particularly, fragments of a feed mined material such as mined ore are supplied to the inlet of the applicator tube and move downwardly as a bed of fragments, typically a packed bed in which the fragments are in contact, of mined material either under gravity feed or forced feed through the applicator tube. The fragments are exposed to microwave radiation in the chamber as the fragments move downwardly through the chamber.

The applicator tube may be any suitable cross-section. A circular cross-section is one suitable cross-section.

The applicator tube may be a wear resistant tube.
The applicator tube may be formed from a wear resistant material.
The applicator tube may include an inner lining of a wear resistant material.

The term "wear resistant" is understood herein in the context of the mined material being processed in the apparatus.

The applicator tube may be at least 150 mm wide at the inlet.

The applicator tube may be at least 200 mm wide at the inlet.

The applicator tube may be at least 500 mm wide at the inlet.

The applicator tube may be at least 250 mm long.

The applicator tube may be at least 1 m long.

The applicator tube may be at least 2 m long.

The apparatus may be adapted to sort at least 100 tonnes per hour of mined material.

The apparatus may be adapted to sort at least 250 tonnes per hour of mined material.

The apparatus may be adapted to sort at least 500 tonnes per hour of mined material.

The apparatus may be adapted to sort at least 1000 tonnes per hour of mined material.

According to the present invention there is provided a method of processing mined material, such as mined ore, including the steps of moving fragments of mined material through the above-described microwave radiation applicator and exposing fragments to microwave radiation.

The method may include processing mined material at a throughput of at least 100 tonnes per hour.

The method may include processing mined material at a throughput of at least 250 tonnes per hour.

The method may include processing mined material at a throughput of at least 500 tonnes per hour.

The method may include processing mined material at a throughput of at least 1000 tonnes per hour.

According to the present invention there is provided a method of sorting mined material, such as mined ore, including the steps of:

(a) moving fragments of mined material through the above-described microwave radiation applicator and exposing fragments to microwave radiation and heating fragments, (b) detecting fragments of mined material after exposing fragments to microwave radiation, (c) using detected data and assessing one or more than one characteristic of fragments, and (d) sorting fragments into multiple streams in response to the assessment of the characteristic(s) of fragments.

The characteristics may include composition (including grade of a valuable metal), mineralogy, hardness, porosity, structural integrity, dielectric properties, and texture of the fragments of mined material.

The mined material may be any mined material that contains valuable material, such as valuable metals. Examples of valuable materials are valuable metals in minerals such as minerals that comprise metal oxides or metal sulphides. Specific examples of valuable materials that contain metal oxides are iron ores and nickel laterite ores. Specific examples of valuable materials that contain metal sulphides are copper-containing ores. Other examples of valuable materials are salt and coal.

Particular, although not exclusive, areas of interest to the applicant are mined material in the form of (a) ores that include copper-containing minerals such as chalcopyrite, in sulphide forms and (b) iron ore.

The present invention is particularly, although not exclusively, applicable to sorting low grade mined material.

The term "low" grade is understood herein to mean that the economic value of the valuable material, such as a metal, in the mined material is only marginally greater than the costs to mine and recover and transport the valuable material to a customer.

In any given situation, the concentrations that are regarded as "low" grade will depend on the economic value of the valuable material and the mining and other costs to recover the valuable material from the mined material at a particular point in time. The concentration of the valuable material may be relatively high and still be regarded as "low" grade. This is the case with iron ores.

According to the present invention there is also provided a method for recovering valuable material, such as a valuable metal, from mined material, such as mined ore, that includes processing mined material according to the method described above and thereafter further processing the fragments and recovering valuable material.

The further processing options for the fragments may be any suitable options, such as smelting and leaching options.

BRIEF DESCRIPTION OF THE DRAWINGS

The present invention is described further by way of example with reference to the accompanying drawings of which.

DESCRIPTION OF EMBODIMENTS

The inventors have carried out a research and development program to design a microwave radiation applicator for use in (a) an automated system for sorting mined material at high throughputs of the material through the applicator and (b) a system for forming microfractures in mined material at high throughputs of the material through the applicator. The research and development program investigated the performance of a number of different applicator designs. It is noted here that, as far as the inventors are aware, there are no commercially available applicator designs for such automated sorting systems and microfracturing systems.

Figure 1:
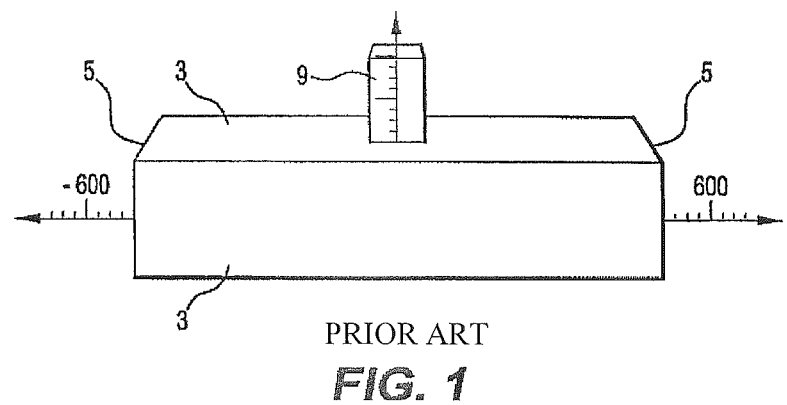
FIG. 1 is a perspective view of a rectangular applicator used in a simulation study carried out by the inventors.

The inventors carried out a simulation study of a particular form of a rectangular applicator shown in FIG. 1 to investigate the potential suitability of the applicator for use in automated sorting systems and microfracturing systems for mined material. This was a logical starting point for the research and development program given that, as noted above, such rectangular applicators are known for domestic microwave heating applications.

The rectangular applicator is illustrated in FIG. 1. With reference to the figure, the rectangular applicator includes four side walls 3 and a pair of end walls 5 that define a chamber. The rectangular applicator is 1000 mm long, 280 mm high, and 800 mm wide and has openings (not shown) in opposite end walls. These openings define an inlet for mined material into the chamber and an outlet for mined material from the chamber. The rectangular applicator also includes an aperture (not shown) in an upper side wall 3 and a vertically-extending waveguide 9 for transmitting microwave radiation from a generator (not shown) into the chamber via the aperture.

In the simulation study the chamber of the rectangular applicator shown in FIG. 1 was exposed to 75 kW microwave radiation supplied to the chamber via the waveguide 9 and the aperture in the upper side wall of the chamber. The simulation study was carried out on a material having average dielectric properties arranged in a horizontal plane. The simulation study calculated the average power density that was incident on the material in the chamber using a numerical simulation. The material was located in a horizontal plane at mid-height of the chamber. This location simulates the location of a conveyor belt transporting mined material through the chamber.

Figure 2:
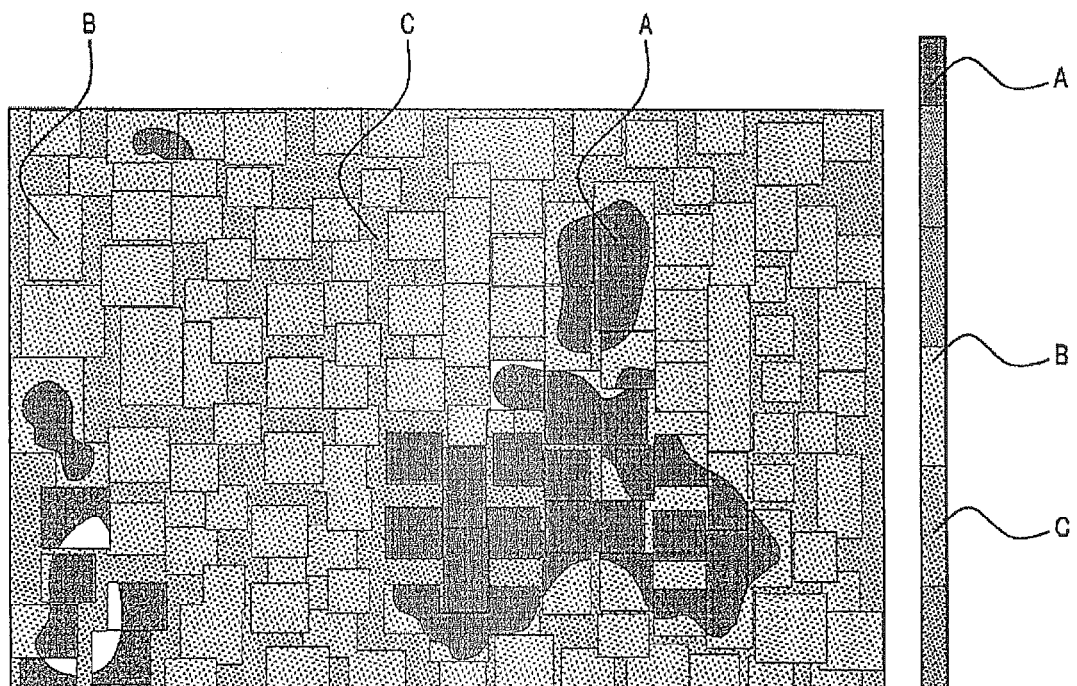
FIG. 2 shows the average power density distribution resulting from the electric field distribution in the chamber of the rectangular applicator shown in FIG. 1 along the length and across the width of the chamber and as viewed from above.

FIG. 2 provides an indication of the exposure of material to microwave radiation in the chamber. In particular, FIG. 2 shows the average power density distribution in the chamber along the length and across the width of the chamber as viewed from above. The Figure is shaded to indicate the power densities—see the scale on the right side of the Figure. The amount of material above a threshold power density of 1 MW/m$^3$ is represented as the most heavily shaded areas in the Figure—see the areas identified by the numeral "A".

The average power density achieved in the rectangular applicator was plotted at a level in the applicator that coincides with a top surface of the smallest fragments of mined material in the applicator under the simulation conditions. This was done in order to include the entire number of fragments considered in the study.

From FIG. 2 it can be seen that there is an extensive variation in the average power density in the material in the rectangular applicator, with the highest values directly under the location of the waveguide feed. Hence, whilst the size of the rectangular applicator is such that a large amount of material can be accommodated in the applicator, it is clear that the heating uniformity was unsatisfactory. More particularly, a substantial amount of material was exposed to power densities below a threshold power density required to provide reliable information on the material to make decisions regarding sorting of the material. Moreover, in a situation in which the applicator is intended for use in a microfracturing system, there would be the same conclusion, namely a substantial amount of material was exposed to power densities below a threshold power density required to provide reliable microcracking of fragments.

Figure 3:
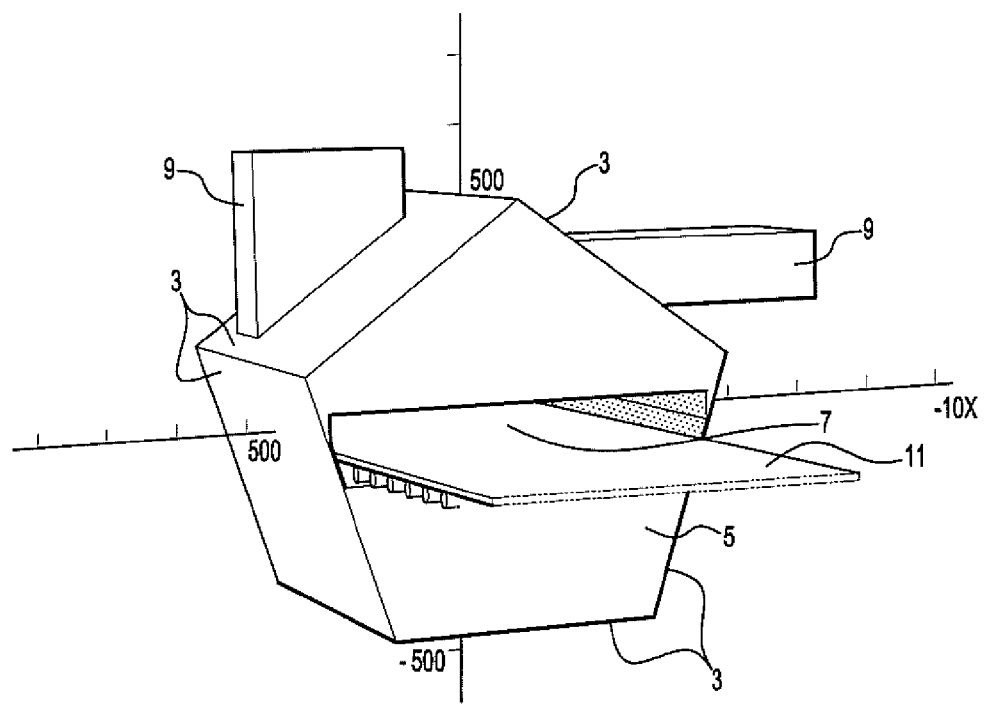
FIG. 3 is a perspective view of one embodiment of a pentagonal multimode applicator in accordance with the present invention.

The inventors simulated the performance of an applicator with side walls that define a pentagon in transverse cross section in accordance with the present invention. With reference to FIG. 3, the embodiment of the pentagonal applicator used in the simulation includes five side walls 3 and a pair of end walls 5 that define a chamber. The pentagonal applicator is arranged with an upper pair of side walls 3 extending downwardly and outwardly from an upper ridge, a lower pair of side walls 3 extending downwardly and inwardly from lower edges of the upper pair of side walls 3, and a horizontally-extending lower side wall 3 interconnecting lower edges of the lower pair of side walls 3. The pentagonal applicator is 1000 mm long and 985 mm wide at its widest point, and has openings 7 in opposite end walls 5 (only one of which is shown in FIG. 3). These openings 7 define an inlet for mined material into the chamber and an outlet for mined material from the chamber. The pentagonal applicator also includes apertures (not shown) in upper side walls 3 and waveguides 9 for transmitting microwave radiation from a generator (not shown) to the apertures. One waveguide 9 extends horizontally and the other waveguide extends vertically from the upper side walls 3. The waveguides 9 are offset longitudinally along the length of the applicator.

When used in an apparatus for sorting mined material, the apparatus may include a horizontally disposed conveyor belt 11 arranged to extend horizontally through the chamber from the inlet to the outlet. Typically, such a conveyor belt is made from a microwave radiation transparent material and may be at least 0.5 m wide and the sorting apparatus may be capable of throughputs of at least 250 tonnes/hr mined material. With this arrangement, the waveguides 9 are above the belt 11.

In the simulation study the pentagonal applicator shown in FIG. 3 was supplied with microwave radiation via the offset pair of waveguides 9 with 37.5 kW in each waveguide. The chamber was exposed to a total of 75 kW microwave radiation via the waveguides. The simulation study was carried out on a material having average dielectric properties. The simulation study calculated the average power density within the material in the chamber using a numerical simulation. The material was located in a horizontal plane at mid-height of the chamber. This location simulates the location of a horizontally-disposed conveyor belt transporting mined material through the chamber.

Figure 4:
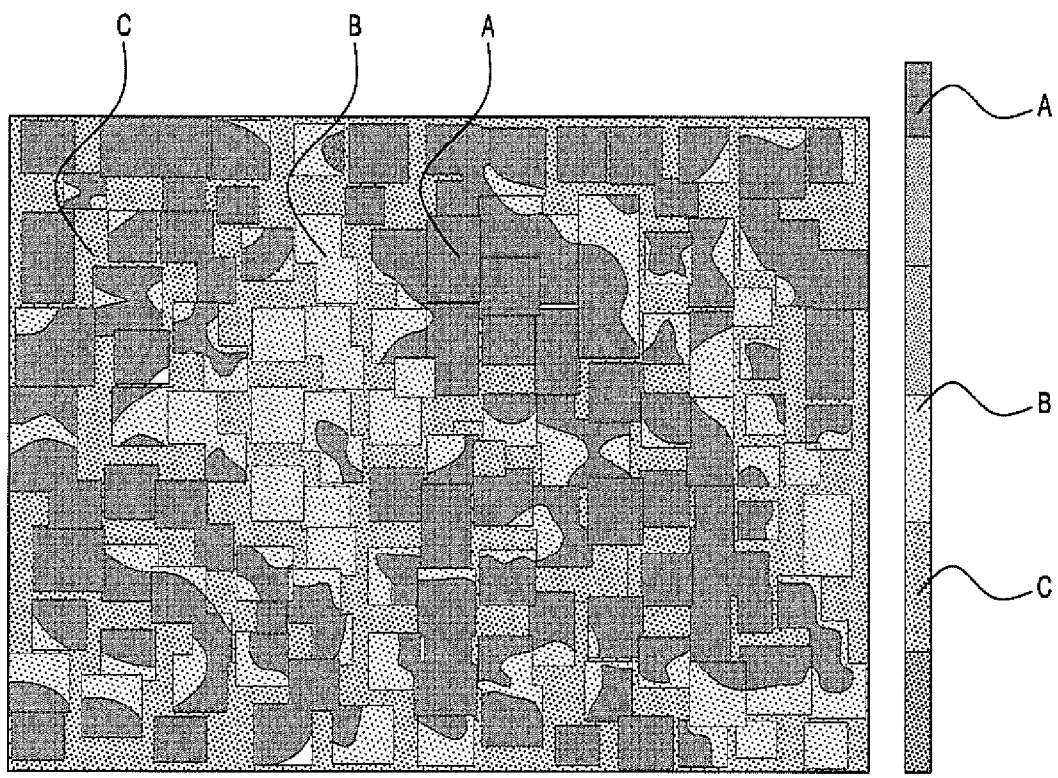
FIG. 4 shows the average power density distribution in the chamber of the pentagonal applicator shown in FIG. 3 along the length and across the width of the chamber and as viewed from above.

FIG. 4 provides an indication of the exposure of material to microwave radiation in the chamber shown in FIG. 3. In particular, FIG. 4 shows the average power density distribution in the chamber along the length and across the width of the chamber as viewed from above. The Figure is shaded to indicate the power densities—see the scale on the right side of the Figure. The amount of material above the threshold of 1 MW/m$^3$ is represented as the most heavily shaded areas in the Figures—see the areas identified by the numeral "A".

The average power density achieved in the applicator was plotted at a level in the applicator that coincides with a top surface of the smallest fragments of mined material in the applicator under the simulation conditions. This was done in order to include the entire number of fragments considered in the study.

More particularly, FIG. 4 shows that a substantial amount of material was exposed to power densities above a threshold power density required to provide reliable information on the material to make decisions regarding sorting of the material. Moreover, in a situation in which the applicator is intended for use in a microfracturing system, there would be the same conclusion, namely a substantial amount of material was exposed to power densities above a threshold power density required to provide reliable microcracking of fragments.

When FIG. 4 is compared to FIG. 2 it can be seen that significantly more of the material exhibits the threshold power density (most heavily shaded regions) with the power density distribution being significantly more uniform when multiple feeds are used in the pentagonal applicator shown in FIG. 3 compared to a single feed in the rectangular applicator. In effect, the results in FIG. 4 when compared with the results in FIG. 2 establish that two microwave feeds (which are perpendicular to each other) and the pentagonal shape maximises the number of modes and that this is a useful result given that field homogeneity (and therefore power density homogeneity) is directly related to the number of modes present.

Figure 5:
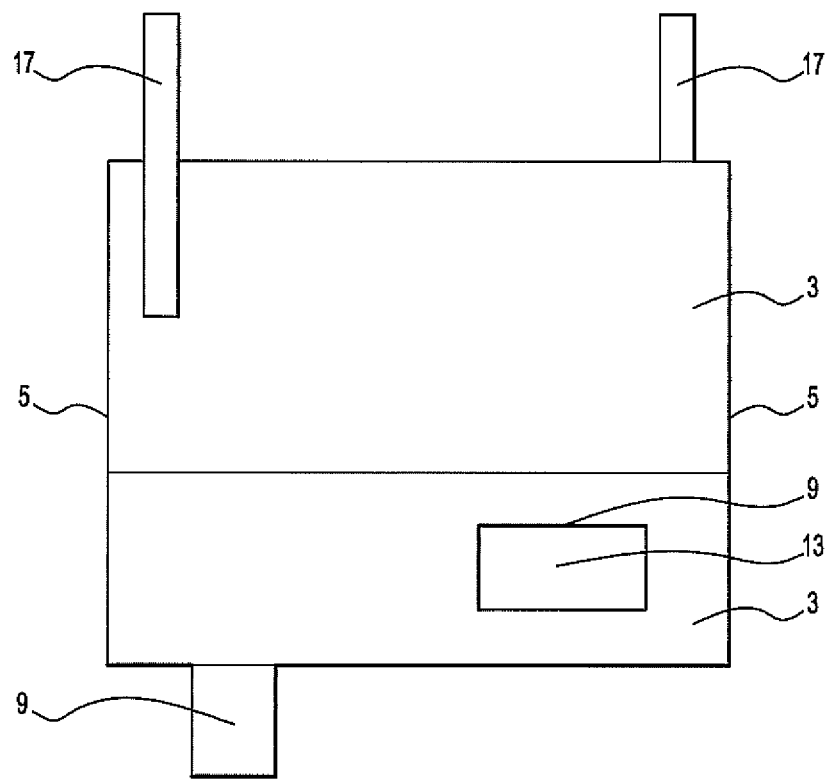
FIG. 5 is a side view of another embodiment of a pentagonal multimode applicator in accordance with the present invention.
Figure 6:
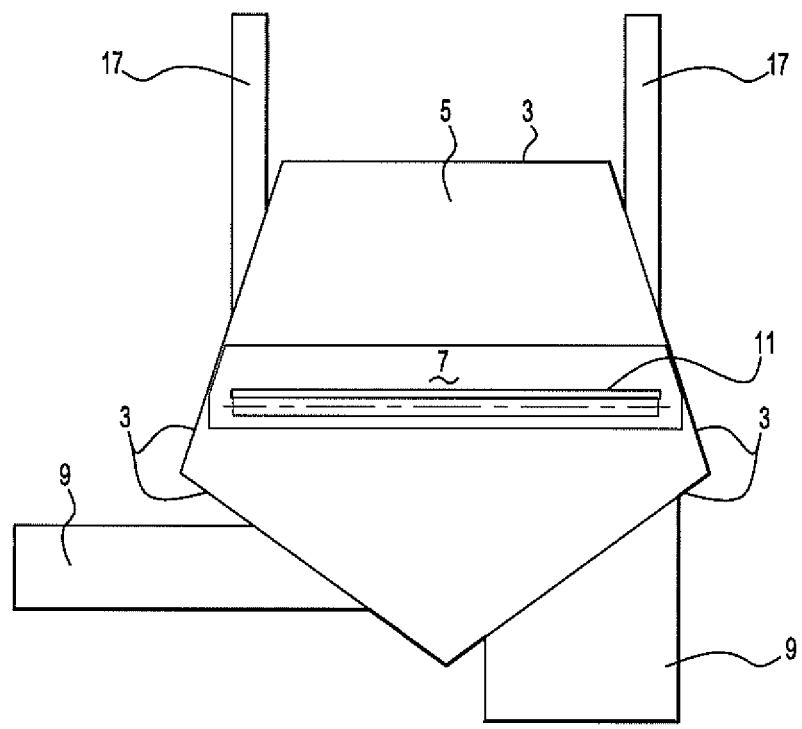
FIG. 6 is an end view of the FIG. 5 pentagonal applicator.

Another embodiment of a pentagonal applicator in accordance with the present invention is shown in FIGS. 5 and 6.

With reference to FIGS. 5 and 6, the pentagonal applicator includes five side walls 3 and a pair of end walls 5 that define a chamber. The pentagonal applicator is arranged with a horizontal upper side wall 3, an upper pair of side walls 3 extending outwardly and downwardly from opposite side edges of the upper side wall 3, and a lower pair of side walls 3 extending inwardly and downwardly from the upper pair of side walls 3 and meeting at lower side edges of the side walls. The pentagonal applicator has openings 7 in opposite end walls 5 (only one of which is shown in FIG. 6). These openings 7 define an inlet for mined material into the chamber and an outlet for mined material from the chamber. The pentagonal applicator is 1000 mm long and 985 mm wide at its widest point and the side walls 3 are each 587.78 mm wide. The openings 7 are 850 mm wide and 150 mm high. The pentagonal applicator also includes apertures 13 (in FIG. 5 only) in the lower pair of side walls 3 and waveguides 9 for transmitting microwave radiation from a microwave radiation generator (not shown). The apertures/waveguides 9 are in both side walls 3 of the lower pair of side walls. The waveguides 9 are offset longitudinally along the length of the application. The waveguides 9 are also offset in terms of the angles of the waveguides 9 in relation to each other. One waveguide 9 is vertical and the other waveguide 9 is horizontal. The pentagonal applicator also has a pair of ventilation apertures in the side walls and ventilation pipes 17 extending from the apertures to allow air flow through the chamber. The apertures/pipes 17 are at opposite ends of the chamber. The apertures/pipes 17 are helpful particularly from the perspective of removing moisture produced in the chamber.

When used in an apparatus for sorting mined material, the apparatus may include a horizontally disposed conveyor belt 11 (see FIG. 6) arranged to extend horizontally through the chamber from the inlet to the outlet. Typically, such a conveyor belt is made from a microwave radiation transparent material. With this arrangement, the waveguides 9 are below the belt 11. This arrangement is advantageous in terms of minimising the amount of dust from mined material that can block the waveguides 9. It is noted that the apertures/waveguides 9 are positioned below the plane of the conveyor belt 11.

The inventors simulated the performance of the pentagonal applicator shown in FIGS. 5 and 6 and obtained results that are similar to the results for the pentagonal applicator shown in FIGS. 3 and 4.

Figure 7:
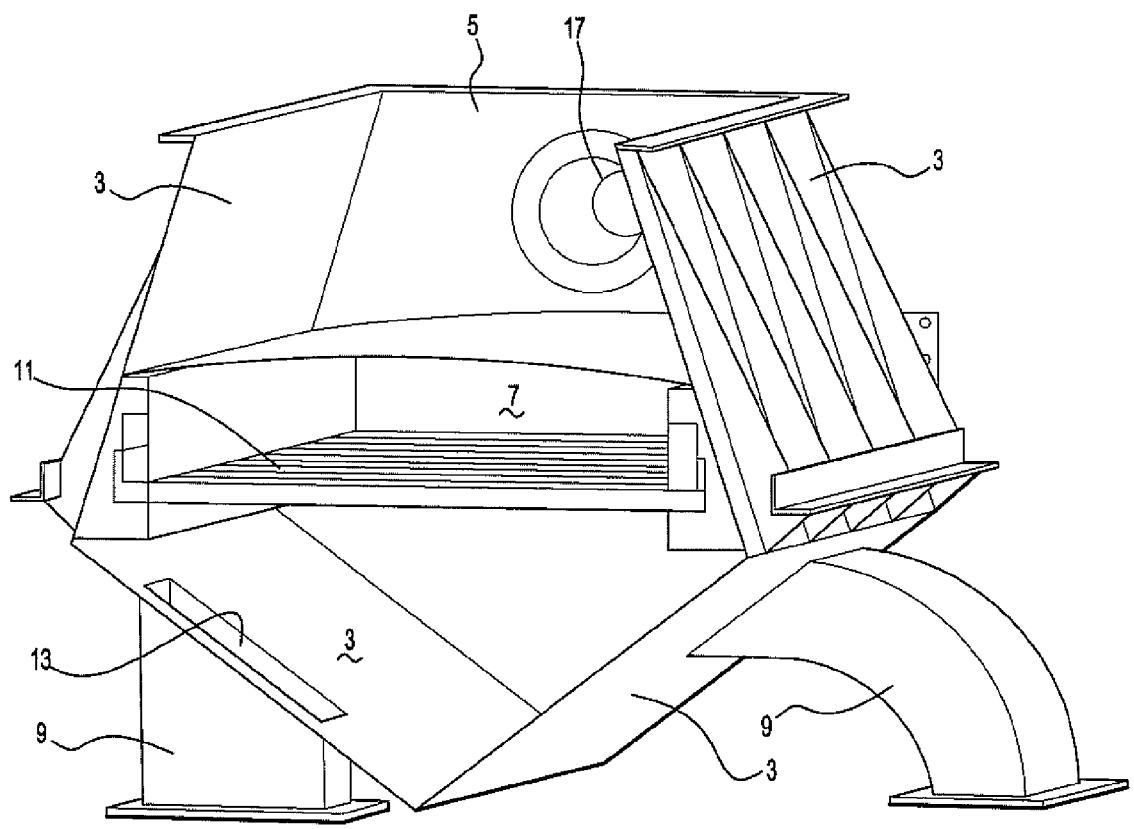
FIG. 7 is a partially cut-away perspective view of another embodiment of a pentagonal multimode applicator in accordance with the present invention.

Another embodiment of a pentagonal applicator in accordance with the present invention is shown in FIG. 7.

With reference to FIG. 7, the pentagonal applicator is the same basic construction as the FIG. 5/6 embodiment and includes five side walls 3 and a pair of end walls 5 that define a chamber. The pentagonal applicator is arranged with a horizontal upper side wall 3, an upper pair of side walls 3 extending outwardly and downwardly from opposite side edges of the upper side wall 3, and a lower pair of side walls 3 extending inwardly and downwardly from the upper pair of side walls 3 and meeting at lower side edges of the side walls. The pentagonal applicator has openings 7 in opposite end walls 5. These openings 7 define an inlet for mined material into the chamber and an outlet for mined material from the chamber. The pentagonal applicator also includes apertures 13 in the lower pair of side walls 3 and waveguides 9 for transmitting microwave radiation from a microwave radiation generator (not shown). The apertures/waveguides 9 are in both side walls 3 of the lower pair of side walls. The waveguides 9 are offset longitudinally along the length of the application. The pentagonal applicator also has a pair of ventilation apertures in the end walls 5 and ventilation pipes 17 extending from the apertures to allow air flow through the chamber. The apertures/pipes 17 are at opposite ends of the chamber. The apertures/pipes 17 are helpful particularly from the perspective of removing moisture produced in the chamber.

Figure 8:
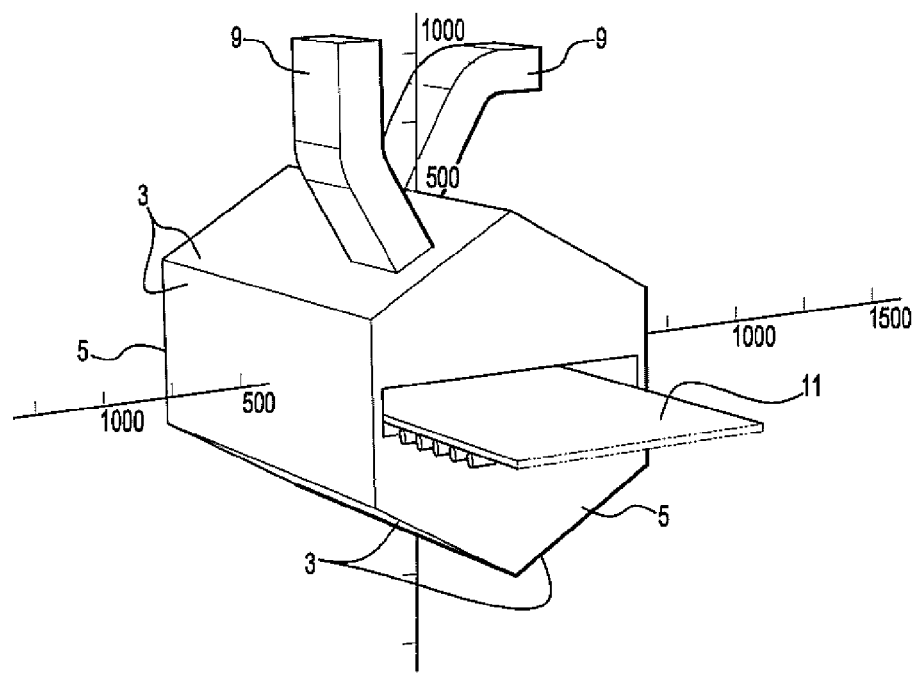
FIG. 8 is a perspective view of a hexagonal multimode applicator investigated by the inventors.

The inventors simulated the performance of an applicator with side walls that define a hexagon in transverse cross section. FIG. 8 shows a representation of the hexagonal applicator. With reference to FIG. 8, the hexagonal applicator includes six side walls 3 and a pair of end walls 5 that define a chamber. The hexagonal applicator is 1000 mm long, 1000 mm high and 1000 mm wide and has openings 7 in opposite end walls. These openings 7 define an inlet for mined material into the chamber and an outlet for mined material from the chamber. The hexagonal applicator also includes apertures (not shown) in upper side walls 3 and waveguides 9 for transmitting microwave radiation from a generator (not shown) that extend perpendicularly from the upper side walls 3. The waveguides are offset longitudinally. The resultant power density distribution inside the chamber is shown as FIG. 9.

Figure 9:
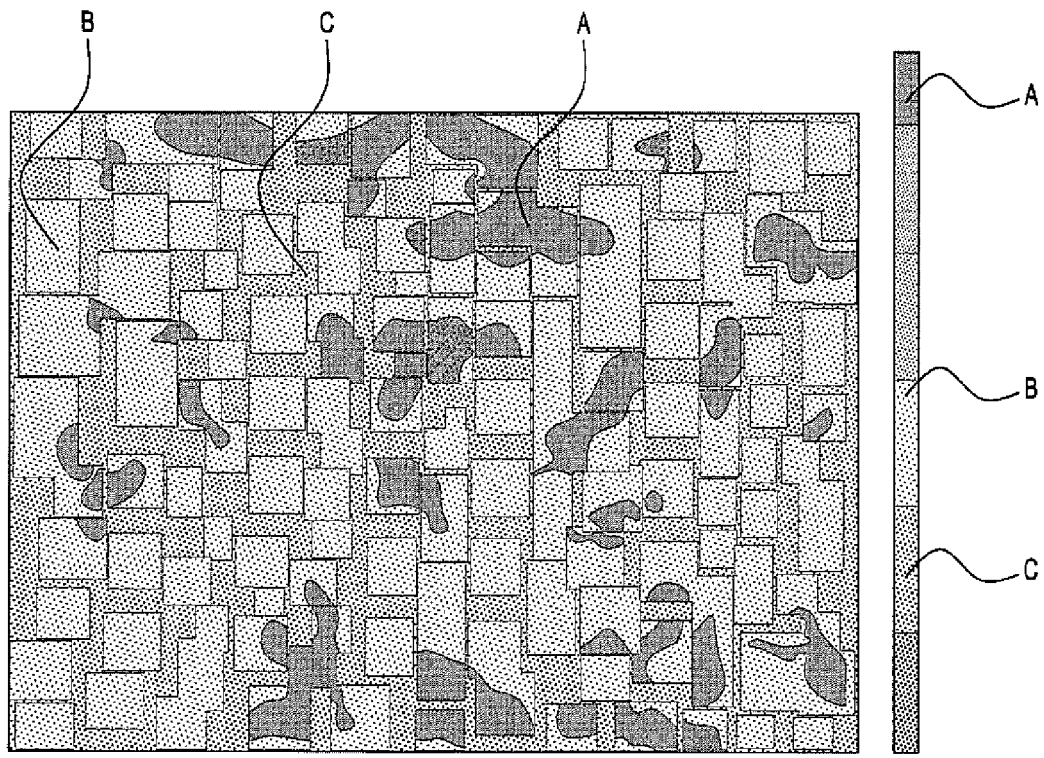
FIG. 9 shows the average power density distribution in the chamber of the hexagonal applicator shown in FIG. 8 along the length and across the width of the chamber and as viewed from above.

It can be seen from FIG. 9 that there is an extensive variation in the average power density inside the material across the width of the applicator, and only a small proportion of the material is above the threshold value of 1 MW/m$^3$. The Figure is shaded to indicate the power densities—see the scale on the right side of the Figure. More particularly, FIG. 9 shows that a substantial amount of material was exposed to power densities below a threshold power density required to provide reliable information on the material to make decisions regarding sorting of the material.

It is evident from the Figures that the hexagonal applicator and the rectangular applicator are not as effective as the pentagonal applicator in terms of making it possible for a substantial amount of material to be exposed to power densities above a threshold power density required to provide reliable information on the material to make decisions regarding sorting of the material.

On the basis of the results of the research and development work described above, the inventors have found that the pentagonal applicator of the present invention provides the following benefits in the context of microwave radiation of mined material or sorting mined material.

High level of assurance that a substantial amount of material processed in the pentagonal applicator would be exposed to power densities above threshold power densities required to microfracture fragments or provide reliable information on the material to make decisions regarding sorting of the material.

Significantly more uniform electric field distribution that can result in very uniform power density when material passes through the applicator.

Higher power density in the heated phase than rectangular and hexagonal applicators for the same power inputs.

Mode stirrers can be used to improve field uniformity even further if required.

Lower electric field strength than horn type applicators that results in lower risk of arcing.

Impedance matching is relatively easy due to the low quality factor of the applicator (Q=stored energy/dissipated energy).

Very flexible design as the pentagonal applicator can accommodate multiple microwave feeds.

Relatively easy to increase residence time and/or thermal difference as overall cavity and residence times are high.

As is indicated above, the applicant is developing an automated sorting system for mined material and the method of sorting mined material being developed by the applicant includes the following steps:

(a) exposing mined material (on a fragment-by-fragment basis or on a bulk basis) to microwave radiation and heating the mined material, (b) detecting fragments of the mined material after the mined material has been exposed to microwave radiation, (c) using detected data and assessing the fragments on the basis of composition (including grade) or texture or another characteristic of the fragments, and (d) physically separating fragments based on the assessment in step (c).

The pentagonal applicators shown in FIGS. 3, 5/6, and 7 are examples of pentagonal applicators in accordance with the invention that are suitable for use in the above described sorting method.

The sorting method is described by way of example below with reference to the sorting apparatus shown in FIGS. 10 and 11.

Figure 10:
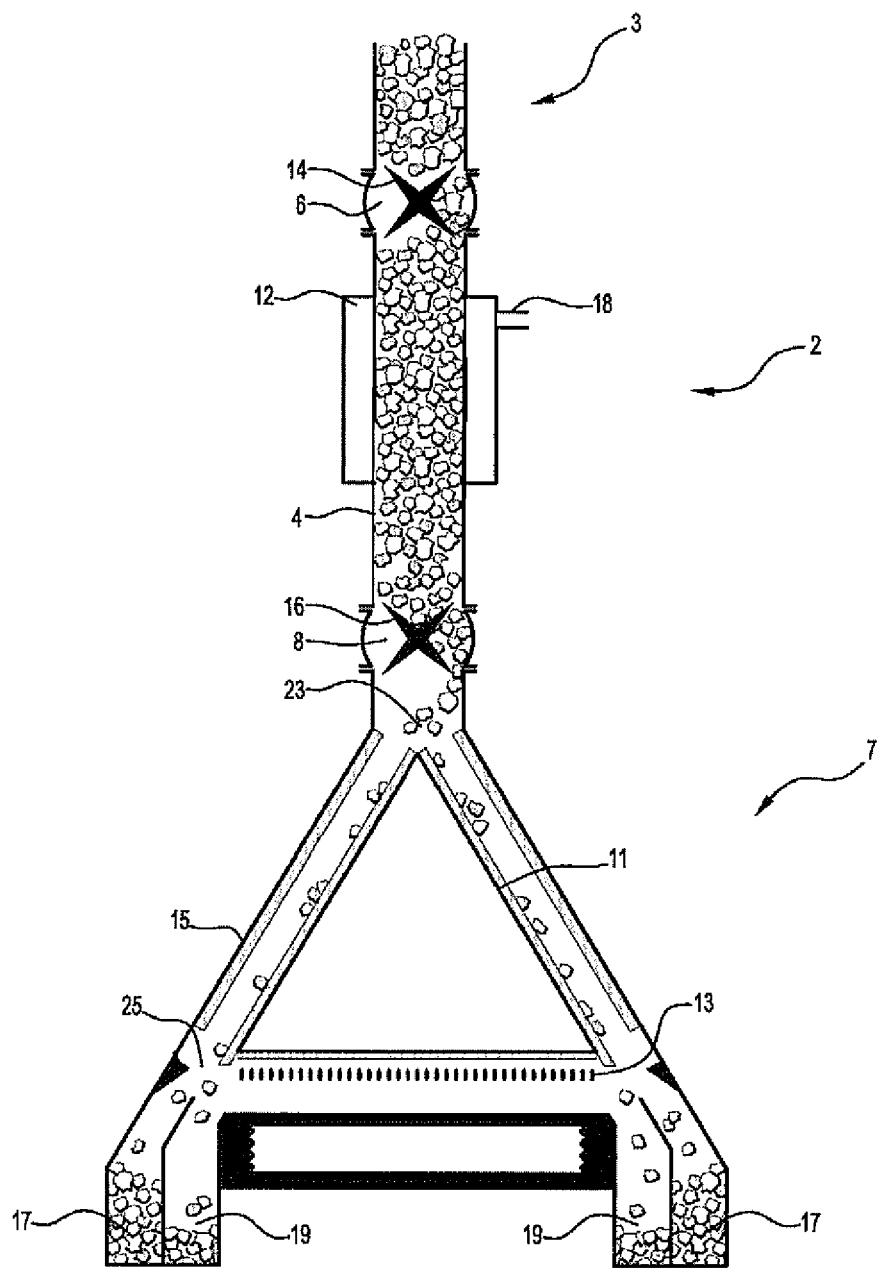
FIG. 10 illustrates diagrammatically a vertical cross-section of one embodiment of key components of a sorting apparatus in accordance with the present invention, which includes an embodiment of a pentagonal multimode applicator in accordance with the present invention.

With reference to FIG. 10, a feed material in the form of fragments of copper-containing ore that have been crushed by a primary crusher (not shown) to a fragment size of 10-25 cm is supplied via a vertical transfer hopper 3 (or other suitable transfer means, such as a conveyor belt supplying material to a feed hopper) to a microwave radiation exposure assembly generally identified by the numeral 2.

The exposure assembly 2 includes (a) a pentagonal applicator 12 such as shown in FIGS. 3, 5/6, and 7 with modified openings in end walls and (b) a materials handling arrangement for transporting fragments of mined material through the chamber of the applicator 12 via the inlet opening in one end wall and the outlet opening in the other end wall.

The materials handling arrangement is in the form of a vertical cylindrical chute or tube 4 that extends through the applicator 12. The ore moves downwardly in a bed, preferably a packed bed moving in plug flow, through the tube 4 from an upper inlet 6 to a lower outlet 8 of the tube 4. The tube 4 is formed from a wear resistant material. By way of example, the tube 4 is formed from a wear resistant ceramic material.

Figure 11:
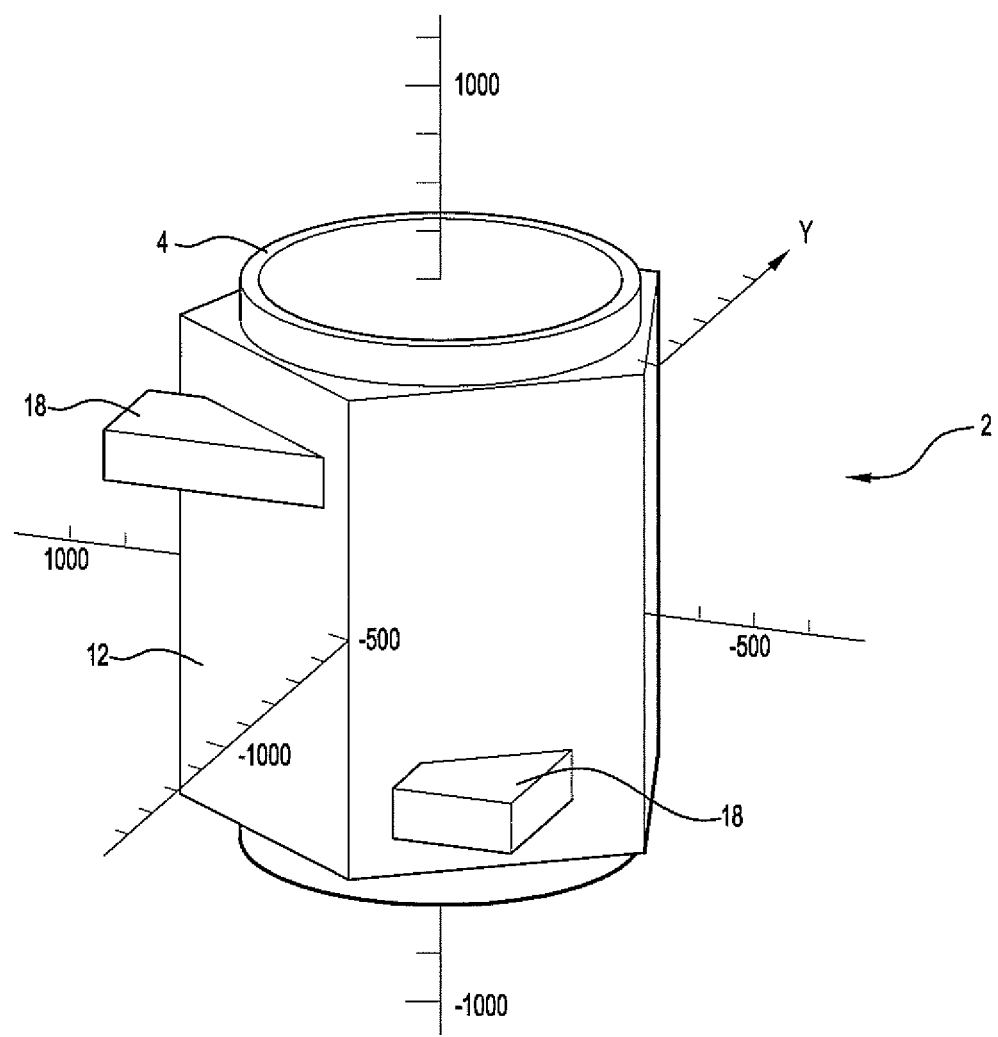
FIG. 11 is a perspective view showing in more detail the embodiment of the applicator shown in FIG. 10.

As can best be seen in FIG. 11, the applicator 12 is pentagonal in transverse cross-section and encloses a section of the tube 4. The applicator 12 is provided for exposing the downwardly moving bed of fragments in the tube 4 to microwave radiation from a source of microwave radiation (not shown). In effect, the tube 4 is positioned to extend through the applicator 12, with the tube 4 physically separating the fragments moving through the tube 4 at any point in time from the applicator 12 and the other components of the exposure assembly 2 that facilitate exposing the fragments to microwave radiation. A section of the tube 4 that is enclosed by the applicator 12 is formed from a microwave transparent material to maximize exposure of the fragments to microwave radiation.

The applicator 12 includes two waveguides 18 for transferring microwave radiation from the source of microwave radiation (not shown) to the applicator 12.

It can be appreciated that the arrangement of the exposure assembly 2 is such that the materials handling requirements for the fragments are at least substantially independent of the electromagnetic radiation exposure requirements for the applicator 12.

The exposure assembly 2 includes chokes 14, 16 for preventing microwave radiation escaping from the tube 4. The chokes 14, 16 are positioned upstream of the inlet 6 and downstream of the outlet 8 of the tube 4. The chokes 14, 16 are in the form of rotary valves in the form of rotatable star wheels in this instance (as shown diagrammatically in FIG. 10) that also control supply and discharge of ore into and from the tube 4.

The outlet 8 of the tube 4 is aligned vertically with an inlet of a fragment distribution assembly. The distribution assembly is generally identified by the numeral 7. The outlet 8 supplies fragments that have been exposed to electromagnetic radiation in the tube 4 directly to the distribution assembly 7.

The distribution assembly 7 includes a distribution surface 11 for the fragments. The fragments move downwardly and outwardly over the distribution surface 11, typically in a sliding and/or a tumbling motion, from an upper central inlet 23 of the distribution assembly 7 to a lower annular outlet 25 of the assembly 7. The distribution surface 11 allows the fragments to disperse from the packed bed state in which the fragments are in contact with each other in the tube 4 to a distributed state in which the fragments are not in contact with other fragments and move as individual, separate fragments and are discharged from the outlet 25 as individual, separate fragments.

The distribution assembly 7 comprises an inner wall having a conical surface that forms the distribution surface 11. The conical surface is an upper surface of a conical-shaped member.

The distribution surface 11 is shrouded by an outer wall having a second concentric outer conical surface 15.

The fragments are detected and assessed by a detection and assessment system as they move through the distribution assembly 7.

More specifically, while passing through the distribution assembly 7, radiation, more particularly heat radiation, from the fragments as a consequence of (a) exposure to microwave energy at the assembly 2 and (b) the characteristics (such as composition and texture) of the fragments is detected by thermal imagers in the form of high resolution, high speed infrared imagers (not shown) which capture thermal images of the fragments. While one thermal imager is sufficient, two or more thermal imagers may be used for full coverage of the fragment surface. It is also noted that the present invention is not limited to detecting the thermal response of fragments to microwave energy and extends to detecting other types of response.

From the number of detected hot spots (pixels), temperature, pattern of their distribution and their cumulative area, relative to the size of the fragments, an estimation of the grade of the fragments can be made. This estimation may be supported and/or more mineral content may be quantified by comparison of the data with previously established relationships between microwave induced thermal properties of specifically graded and sized fragments.

Images collected by the thermal imagers and the visible light cameras (and information from other sensors such as visible light cameras that may be used) are processed in the detection and assessment system by a computer (not shown)

equipped with image processing and other relevant software. The software is designed to process the sensed data to assess the fragments for sorting and/or downstream processing options. In any given situation, the software may be designed to weight different data depending on the relative importance of the properties associated with the data.

The detection and assessment system generates control signals to selectively activate a sorting means in response to the fragment assessment.

More specifically, the fragments free-fall from the outlet 25 of the distribution assembly 7 and are separated into annular collection bins 17, 19 by a sorting means that comprises compressed air jets that selectively deflect the fragments as the fragments move in a free-fall trajectory from the outlet 25 of the distribution assembly 7. The air jet nozzles are identified by the numeral 13. The air jets selectively deflect the fragments into two circular curtains of fragments that free-fall into the collection bins 17, 19. The thermal analysis identifies the position of each of the fragments and the air jets are activated a pre-set time after a fragment is analysed as a fragment to be deflected.

The positions of the thermal imagers and the other sensors and the computer and the air jets may be selected as required. In this connection, it is acknowledged that FIG. 10 is not intended to be other than a general diagram of one embodiment of the invention.

The microwave radiation may be either in the form of continuous or pulsed radiation. The microwave radiation may be applied at an electric field below that which is required to induce micro-fractures in the fragments. In any event, the microwave frequency and microwave intensity and the fragment exposure time and the other operating parameters of the assembly 2 are selected having regard to the information that is required. The required information is information that is required to assess the particular mined material for sorting and/or downstream processing of the fragments.

In one mode of operation the thermal analysis is based on distinguishing between fragments that are above and below a threshold temperature. The fragments can then be categorised as "hotter" and "colder" fragments. The temperature of a fragment is related to the amount of copper minerals in the fragment. Hence, fragments that have a given size range and are heated under given conditions will have a temperature increase to a temperature above a threshold temperature "x" degrees if the fragments contain at least "y" wt. % copper. The threshold temperature can be selected initially based on economic factors and adjusted as those factors change. Barren fragments will generally not be heated on exposure to radio frequency radiation to temperatures above the threshold temperature.

In the present instance, the primary classification criteria is the grade of the copper in the fragment, with fragments above a threshold grade being separated into collection bin 19 and fragments below the threshold grade being separated into the collection bin 17. The valuable fragments in bin 19 are then processed to recover copper from the fragments. For example, the valuable fragments in the bin 19 are transferred for downstream processing including milling and flotation to form a concentrate and then processing the concentrate to recover copper.

The fragments in collection bin 17 may become a by-product waste stream and are disposed of in a suitable manner. This may not always be the case. The fragments have lower concentrations of copper minerals and may be sufficiently valuable for recovery. In that event the colder fragments may be transferred to a suitable recovery process, such as leaching.

Many modifications may be made to the embodiment of the present invention described above without departing from the spirit and scope of the invention.

By way of example, whilst the embodiments of the pentagonal applicator shown in FIGS. 3 and 5/6 and 7 and 10/11 have transverse cross-sections in the form of regular pentagons, the present invention is not so limited and extends to arrangements in which the cross-sections are irregular pentagons.

By way of example, whilst the embodiments of the sorting apparatus in accordance with the present invention that includes the pentagonal applicators shown in FIGS. 3/4 and 5/6 and 7 are described as including conveyor belts to transport mined material through the applicators, the present invention is not so limited and extends to other options for moving mined material through the applicators. For example, as is shown in FIGS. 10/11, the apparatus may include an applicator tube for containing a bed of mined material that extends through the applicator from the inlet to the outlet in the end walls of the applicator. This arrangement has an advantage over belt arrangements of decoupling materials handling issues and microwave radiation exposure issues.

In addition, whilst the embodiments of the applicator of the invention shown in the Figures relate to sorting mined material, the invention is not limited to this use of the applicators and the invention extends to using the applicators generally for processing mined material. One other particular application of interest to the applicant is for microfracturing fragments of mined material.

The invention claimed is:

1. An apparatus for sorting mined material that includes:
   (a) a microwave radiation generator for generating microwave energy;
   (b) a microwave radiation applicator for heating mined material spaced away from the microwave radiation generator, the applicator including side walls and end walls that define a chamber, with one end wall having an opening that forms an inlet for mined material to be supplied to the chamber and the other end wall having an opening that defines an outlet for mined material to be discharged from the chamber, with the side walls defining a pentagon in transverse cross-section, the applicator including at least one aperture in the side walls to allow transmission of microwave radiation into the chamber and a waveguide for transmitting microwave radiation from the microwave radiation generator to the aperture;
   (c) a materials handling arrangement for transporting fragments of mined material through the chamber via the inlet in one end wall and the outlet in the other end wall,
   (d) a detector for detecting fragments of mined material after exposure to microwave radiation,
   (e) a means for analysing data from the detector and assessing one or more than one characteristic of fragments, and
   (f) a means for separating the fragments on the basis of the analysis.

2. The apparatus defined in claim 1 wherein the materials handling arrangement for transporting fragments of mined material within the chamber is arranged to transport fragments horizontally through the applicator.

3. The apparatus defined in claim 1 wherein the applicator includes one aperture only to allow transmission of microwave radiation into the chamber.

4. The apparatus defined in claim 1 wherein the applicator includes a plurality of apertures so that the applicator can operate as a multimode applicator.

5. The apparatus defined in claim 4 wherein the applicator includes a plurality of waveguides for transmitting microwave radiation from the microwave radiation generator into the chamber via the apertures.

6. The apparatus defined in claim 4 wherein the apertures are in one of the side walls.

7. The apparatus defined in claim 4 wherein the apertures are in more than one of the side walls.

8. The apparatus defined in claim 4 wherein the waveguides are offset with respect to each other.

9. The apparatus defined in claim 4 wherein the apertures are above and below the materials handling arrangement.

10. The apparatus defined in claim 1 wherein the side walls of the applicator include a horizontal upper side wall, an upper pair of side walls extending outwardly and downwardly from opposite side edges of the upper side wall, and a lower pair of side walls extending inwardly and downwardly from the upper pair of side walls and meeting at lower side edges of the side walls.

11. The apparatus defined in claim 1 wherein the side walls of the applicator include a horizontal lower side wall, a lower pair of side walls extending outwardly and upwardly from opposite side edges of the lower side wall, and an upper pair of side walls extending inwardly and upwardly from the lower pair of side walls and meeting at upper side edges of the side walls.

12. The apparatus defined in claim 1 wherein the pentagon is a regular pentagon.

13. The apparatus defined in claim 1 wherein the pentagon is an irregular pentagon.

14. The apparatus defined in claim 1 wherein the materials handling arrangement includes a belt for transporting fragments of mined material through the chamber.

15. The apparatus defined in claim 1 wherein the applicator is arranged so that, in use, fragments of mined material can be transported vertically or at an angle to the vertical through the applicator, with the side walls being vertical or angled side walls and one end wall being an upper end wall and the other end wall being a lower end wall.

16. The apparatus defined in claim 15 wherein the materials handling arrangement includes an applicator tube for transporting a bed of fragments of mined material downwardly through the chamber from the upper end wall to the lower end wall, and the applicator tube physically separating the fragments moving through the applicator from the chamber so that the materials handling requirements for the fragments in the applicator are at least substantially independent of the microwave radiation exposure requirements for the applicator.

17. A method of processing mined material including the steps of moving fragments of mined material through the microwave radiation applicator of the apparatus defined in claim 1 and exposing fragments to microwave radiation.

18. A method of sorting mined material including the steps of:
(a) moving fragments of mined material through the microwave radiation applicator of the apparatus defined in claim 1 and exposing fragments to microwave radiation and heating fragments,
(b) detecting fragments of mined material after exposing fragments to microwave radiation,
(c) using detected data and assessing one or more than one characteristic of fragments, and
(d) sorting fragments into multiple streams in response to the assessment of the characteristic(s) of the fragments.

* * * * *